(12) United States Patent
Gehrke et al.

(10) Patent No.: US 6,853,195 B2
(45) Date of Patent: Feb. 8, 2005

(54) DEVICE AND PROCESS FOR MEASUREMENT OF THE CONCENTRATION OF IONS IN A MEASUREMENT LIQUID

(75) Inventors: Martin Gehrke, Weinstadt (DE); Detlev Wittmer, Maulbronn (DE)

(73) Assignee: Endress + Hauser Conducta Gesellschaft fur Mess und Regeltechnik mbH + Co., Gerlingen (DE)

( * ) Notice: Subject to any disclaimer, the term of this patent is extended or adjusted under 35 U.S.C. 154(b) by 129 days.

(21) Appl. No.: 10/116,113

(22) Filed: Apr. 5, 2002

(65) Prior Publication Data

US 2002/0171430 A1 Nov. 21, 2002

(30) Foreign Application Priority Data

Apr. 7, 2001 (DE) .......................................... 101 17 627

(51) Int. Cl.[7] ............................................ G01N 27/416
(52) U.S. Cl. ........................ 324/438; 324/459; 324/464
(58) Field of Search ................................. 324/438, 459, 324/464

(56) References Cited

U.S. PATENT DOCUMENTS

| | | | | | |
|---|---|---|---|---|---|
| 4,506,226 A | * | 3/1985 | Luce et al. | .................. | 324/459 |
| 5,267,569 A | * | 12/1993 | Lienhard | .................... | 600/504 |

* cited by examiner

Primary Examiner—N. Le
Assistant Examiner—Vincent Q. Nguyen
(74) Attorney, Agent, or Firm—Hoffman, Wasson & Gitler PC

(57) ABSTRACT

A symmetrically wired device and a process for measurement of the concentration of ions, especially hydrogen (H+) ions, in a measurement liquid. The device comprises a pH-sensitive measurement electrode, a reference electrode and a comparison electrode, all located in the measurement liquid and which places the measurement liquid at a definable ground reference. The device forms a difference signal referenced to the ground reference from the difference between a measurement signal ($\phi$pH) of the measurement electrode and the reference signal ($\phi$ref) of the reference electrode. The difference signal is dependent on the ion concentration in the measurement liquid. The device compensates for the noise potential ($\phi$chem) arising between the comparison electrode and the measurement electrode by setting a reference potential ($\phi$bez) on the comparison electrode, such that $\phi$ref assumes a zero value.

5 Claims, 3 Drawing Sheets

DEVICE AND PROCESS FOR MEASUREMENT OF THE CONCENTRATION OF IONS IN A MEASUREMENT LIQUID

BACKGROUND OF THE INVENTION

1. Field of the Invention

This invention relates to a symmetrically wired device for measurement of the concentration of ions, especially hydrogen ($H^+$) ions, in a measurement liquid.

2. Description of the Prior Art

The prior art discloses measurement devices for measurement of the ion concentration in a measurement liquid in different embodiments. Thus the pH of a measurement liquid can be recorded via asymmetrically wired measurement chains or via symmetrically wired measurement chains. The asymmetrically wired measurement chain comprises a reference electrode which is at the ground reference which is located in the measurement liquid and a pH-sensitive measurement electrode which is located in the measurement liquid, for example a glass electrode or a semiconductor electrode. A measurement signal referenced to the ground reference is recorded at the output of the measurement electrode. The measurement signal is dependent on the ion concentration in the measurement liquid.

A symmetrically wired device known from the prior art for measurement of the ion concentration is labeled in its totality with reference number 1 in FIG. 2. The device 1 comprises a pH-sensitive measurement electrode 3 which is located in the measurement liquid 2, a reference electrode 4 located in the measurement liquid 2, and a comparison electrode 5 located in the measurement liquid 2. The measurement liquid 2 is placed at a definable ground reference GND by the comparison electrode 5. The device furthermore comprises a subtractor 6 for forming a difference signal $\phi pH$ which is referenced to the ground reference GND from the difference between the measurement signal $\phi pH$ of the measurement electrode 3 and the reference signal $\phi ref$ of the reference electrode 4. The difference signal UpH is dependent on the ion concentration in the measurement liquid 2 or the pH of the measurement liquid 2. The measurement signal $\phi pH$ and the reference signal $\phi ref$ are made as potentials. They are each routed via operational amplifiers 7, 8 wired as an impedance converter or isolation amplifier. The output signal of the subtractor 6 is likewise routed via an operational amplifier 9 which is wired as an impedance converter or isolation amplifier. The operational amplifiers 7, 8, 9 are used for common mode rejection, i.e. to reduce the fault susceptibility of the device 1. A conventional operational amplifier has common mode rejection of roughly 80 to 90 dB. This means that at an assumed allowable error at the output of an operational amplifier of 1 mV, at the input, a voltage fluctuation of up to 10 V can occur.

In the device known from the prior art for measurement of the pH of a measurement liquid, voltage fluctuations are caused for example by electrochemical noise potentials which arise between the comparison electrode and the measurement liquid, or by other disturbances which are coupled for example onto the measurement line. The magnitude of the noise potential is dependent on the material of the comparison electrode used and on the composition of the measurement liquid. The comparison electrode consists for example of high quality steel or of tantalum. The noise potential is added to the measurement signal and the reference signal equally. The difference formation provided in the symmetrical wiring eliminates the noise potential so that it does not act on the output signal of the device. The noise potential however leads to a rise in the individual potentials which are to be processed in the isolation amplifiers. The noise potential enters directly into the control range of the isolation amplifiers for the two potentials and in the following substructure. The electrochemical offset can be up to +/−1.4 V, in extreme cases even up to +/−2.8 V.

The increasing miniaturization of electronic components, especially to reduce the heat loss of active components, is generally accompanied by a reduction of the power supply voltage as well. Modern ASICs (Application Specific Integrated Circuits) for example are operated with power supply voltages which are Vcc=3 V or even less. In these circuits, the common mode range is limited to +/−3 V. When there is a noise potential or an electrochemical offset in the range of the power supply voltage, in the course of measurement of the pH the common mode range can be exceeded. The input circuit is then no longer able to linearly transmit the difference voltage and major measurement deviations can occur. In addition, the measurement signal can reach the trigger limit and can be simply cut off at a certain value, for example 3 V. For the case in which an analog subtraction circuit forms the difference of the two potentials, a following measurement instrument or a following A/D converter cannot detect any difference between a pH which is becoming smaller and a clipping of the potentials. A measurement is no longer possible.

SUMMARY OF THE INVENTION

The device according to the present invention comprises a pH-sensitive measurement electrode located in a measurement liquid, a reference electrode located in the measurement liquid, a comparison electrode which is located in the measurement liquid and which places the measurement liquid at a definable ground reference, and a means for forming a difference signal referenced to the ground reference from the difference between the measurement signal of the measurement electrode and the reference signal of the reference electrode. The difference signal is dependent on the ion concentration in the measurement liquid.

The invention also relates to a process for measurement of the concentration of ions, especially hydrogen ($H^+$) ions in a measurement liquid. Within the framework of the process, one measurement signal is received by the pH-sensitive measurement electrode located in the measurement liquid, and one reference signal is received by the reference electrode located in the measurement liquid. The measurement liquid is placed at a definable ground reference by the comparison electrode located in the measurement liquid. A difference signal which is dependent on the ion concentration in the measurement liquid and which is referenced to the ground reference is formed from the difference between the measurement signal and the reference signal.

Finally, this invention relates to a storage element for a control unit of a device for measurement of the concentration of ions, especially hydrogen ($H^+$) ions in a measurement liquid. The storage element stores a computer program which can run on an arithmetic device, especially a microprocessor of the control unit. The storage element is made especially as a read-only memory, as a random-access memory or as a flash memory.

Measurement devices of the initially mentioned type are ordinarily used to measure the pH of a measurement liquid. The pH is determined by a host of ingredients dissolved in the measurement liquid, for example by the concentration of $H^+$ ions or OH− ions.

An object of this invention is, in spite of small power supply voltages of the electrical components, especially at a power supply voltage of less than 4 V, to enable accurate and reliable measurement of the pH in a measurement liquid with a symmetrically wired pH measurement device.

To achieve this object, for a measurement device of the initially mentioned type, as claimed in the invention, a compensation means for compensation of the noise potential which arises between the comparison electrode and the measurement liquid is proposed.

Using the compensation means, it is possible to counteract a significant cause of clipping, specifically reaching the power supply voltage limit. The noise potential can be compensated by the reference potential on the comparison electrode being set to the negative noise potential. Alternatively, however compensation can also take place by the sum of the reference potential and the noise potential being set such that the reference signal or the measurement signal becomes zero. Since the modulation of the comparison electrode can take place up to the negative power supply voltage limit, and the measurement signal and the reference signal can travel as far as the positive supply limit, the common mode detection range can be almost doubled by this invention, without a change being necessary on the power supply voltage.

According to one advantageous development of this invention, it is proposed that the compensation means sets the reference potential on the comparison electrode depending on the noise potential. The potential on the comparison electrode arises from the sum of the reference potential and the noise potential. Preferably the reference potential is adjusted to the negative noise potential. According to this development the reference potential can be set such that the noise potential is compensated and only a reference potential of 0 V (ground) is on the comparison electrode in the ideal case.

According to another advantageous development of this invention, it is proposed that the compensation means sets the reference potential on the comparison electrode such that the reference signal assumes a definable value. Advantageously, the compensation means sets the reference potential such that the reference signal assumes a value of zero. The reference signal is preferably adjusted to a definable value by varying the reference potential depending on the noise signal.

To control the reference signal it is proposed that the compensation means comprises a controller element for adjusting the reference potential on the comparison electrode to a definable setpoint, the reference signal being present as the actual value and the setpoint being on the controller element.

According to another preferred embodiment of this invention, it is proposed that the controller element is made as an operational amplifier, the reference signal is at its noninverting input, the ground reference is at its inverting input and the reference potential is at its output.

The object of this invention is furthermore achieved proceeding from the process of the initially mentioned type by compensating the noise potential which arises between the comparison electrode and the measurement liquid.

According to one advantageous development of the invention, it is proposed that the reference potential on the comparison electrode is set depending on the noise potential. According to one preferred embodiment of this invention, it is proposed that the reference potential on the comparison electrode is set such that the reference signal assumes a definable value. The reference potential is advantageously set such that the reference signal assumes a value of zero.

According to another preferred embodiment of this invention, it is proposed that the reference potential on the comparison electrode is controlled depending on the reference signal as the actual value and a definable setpoint.

The implementation of the process is the form of a storage element, which is intended for a control unit of a device for measurement of the concentration of ions, especially hydrogen ($H^+$) ions in a measurement liquid, is of special importance. The storage element stores a computer program which can run on an arithmetic device, especially a microprocessor of the control unit, and is suited for execution of the process as claimed in the invention. In this case, therefore the invention is implemented by a computer program stored on the storage element so that this storage element which is provided with the computer program represents the invention, like the process which the computer program is suited to execute. The storage element can be especially an electrical storage medium, for example a read-only memory, a random-access memory or a flash memory.

Other features, possible applications and advantages of the invention result from the following description of embodiments of the invention which are shown in the drawings. All the described features in and of themselves or in any combination form the subject matter of the invention, regardless of their composition in the claims or their referencing and regardless of their formulation or description in the specification and in the drawings.

DETAILED DESCRIPTION OF THE INVENTION

Figure 2:
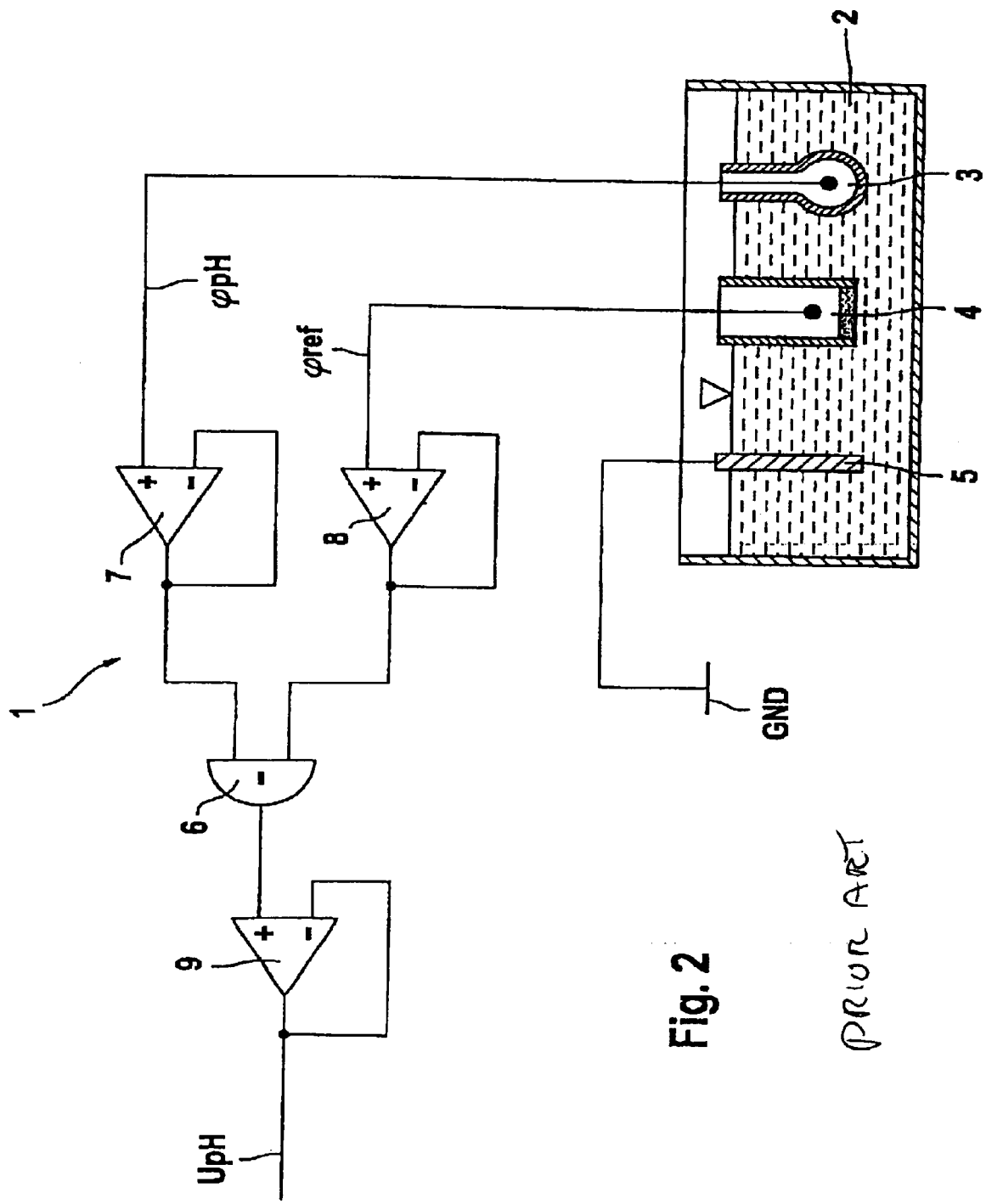
FIG. 2 shows a device for measurement of the ion concentration in a measurement liquid known from the prior art.

A device 1 known from the prior art for measurement of the ion concentration in a measurement liquid 2 is described in detail in the introductory part of the specification using FIG. 2. The measurement device 1 is used to measure the pH in the measurement liquid 2. The pH is determined by a host of ingredients dissolved in the measurement liquid 2, for example by the concentration of $H^+$ ions or $OH^-$ ions.

In the known device 1, based on the electrochemical noise potentials between the comparison electrode 5 and the measurement liquid 2, the signals φpH and φref which are to be processed in the isolation amplifiers 7, 8 and 9 and the output signal from the subtractor 6 are raised by the noise potential φchem which arises. The noise potential φchem can be in the range of roughly +/−1.4 V, in extreme cases even in the range of +/−2.8 V. Based on the noise potential φchem, at low power supply voltages, especially at power supply voltages of less than 4 V, it can happen that the signals φpH, φref and/or the output signal from the subtractor 6 reach the power supply voltage limit and are simply cut off (so-called clipping). For the case in which an analog subtraction circuit forms the difference of the two potentials φpH, φref, a following measuring instrument or a following A/D converter cannot detect the difference between a pH which is becoming smaller and the clipping of the potentials φpH, φref. Then measurement is no longer possible.

Figure 1:
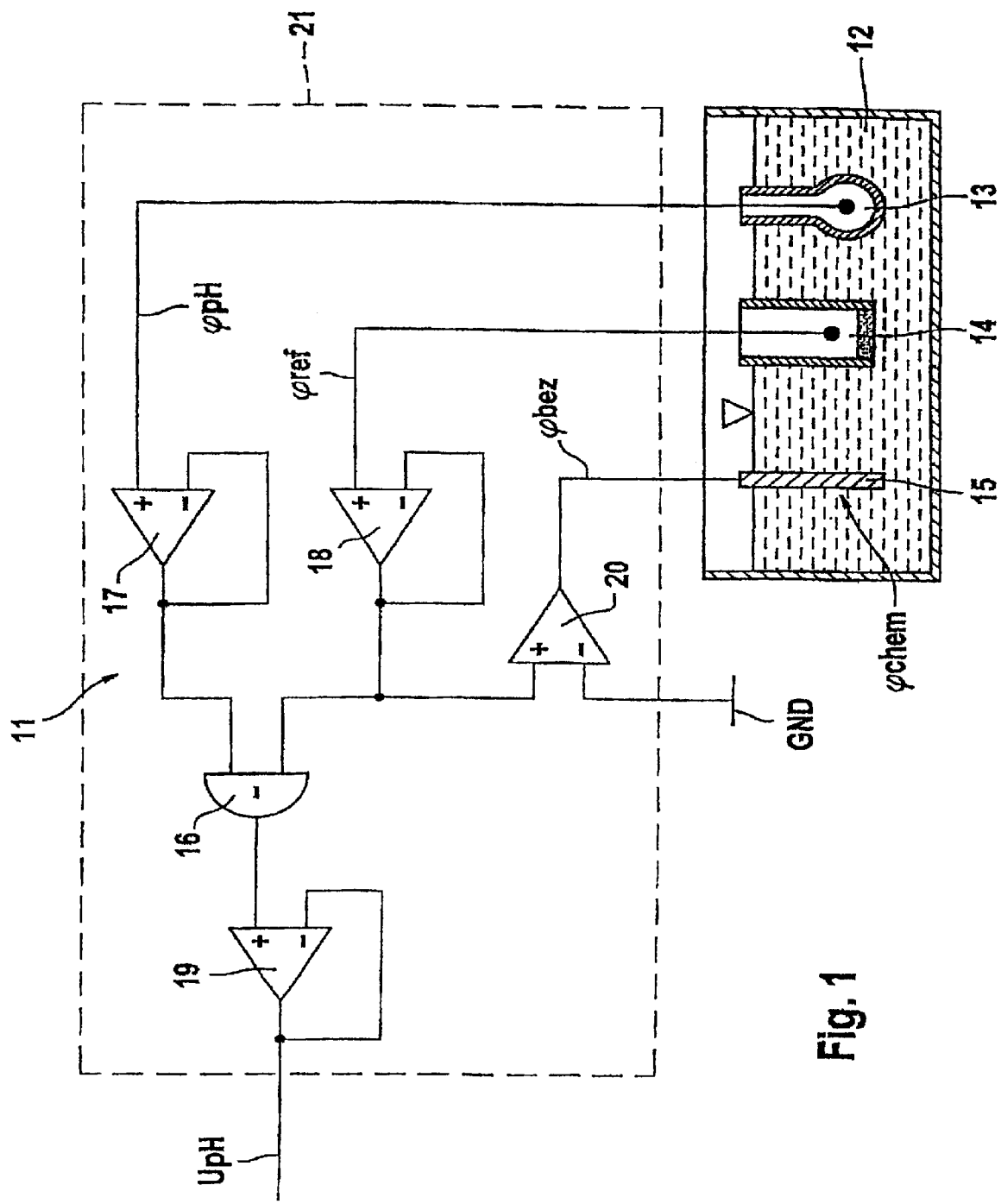
FIG. 1 shows a device for measurement of the ion concentration in a measurement liquid.

To prevent these problems at low power supply voltages, a measurement device 11 which is shown in FIG. 1 is proposed. The device 11 comprises a pH-sensitive measurement electrode 13 located in a measurement liquid 12, a reference electrode 14 located in the measurement liquid 12, and a comparison electrode 15 which is located in the measurement liquid 12. The measurement electrode 13 is also called a pH half cell and the reference electrode 14 is called a reference half cell. The comparison electrode 15 is also called a potential equalization line (PAL). The measurement liquid 12 is placed at a definable reference potential by the comparison electrode 15.

The device 11 furthermore comprises a subtractor 16 for forming a difference signal UpH which is referenced to the ground reference from the difference between the measurement signal φpH of the measurement electrode 13 formed as a potential and a reference signal φref of the reference electrode 14 likewise formed as a potential. Subtraction can eliminate noise effects so that they do not affect the difference signal Uph. This yields high invulnerability of the measurement device 11 to interference. The difference signal UpH is dependent on the ion concentration in the measurement liquid 12 or the pH of the measurement liquid 12. The measurement signal φpH and the reference signal φref are formed as potentials. They are each routed via an operational amplifier 17, 18 which is wired as an impedance converter or an isolation amplifier. The output signal of the subtractor 16 is likewise routed via an operational amplifier 19 which is wired as an impedance converter or isolation amplifier. The operational amplifiers 17, 18, 19 are used for common mode rejection, i.e. to reduce the fault susceptibility of the device 11.

In the device 11 from FIG. 1 a reference potential φbez on the comparison electrode 15 is adjusted depending on the noise potential φchem such that the reference signal φref assumes a value of zero. To do this, the device 11 has a controller element which is made as an operational amplifier 20; the reference signal φref is at its noninverting input (+), the ground reference GND is at its inverting input (−) and the reference potential φbez is at its output.

The reference potential φbez is therefore corrected in the opposite direction to the electrochemical noise potential φchem. In this way the cause of clipping, specifically reaching the power supply voltage limit of the operational amplifiers 17, 18, and 20, can be effectively counteracted as a result of the potential increase of the measurement signal φpH caused by the noise potential φchem, of the reference signal φref and of the output signal of the subtractor 16. To control the reference potential φbez, the reference potential φref on the reference electrode 14 is defined as 0 V. The reference potential φref is supplied as the actual value to the noninverting input (+) of the operational amplifier 20. The ground reference GND as the setpoint of 0 V is on the inverting input (−) of the operational amplifier 20. The output of the controller element 20 operates the comparison electrode 15.

During operation of the device 11 a potential is established on the electrical terminal of the comparison electrode 15 such that the electrical terminal of the reference electrode 14 is 0 V. Thus, an ideally offset-free, pH-proportional measurement signal φpH is available on the terminal of the measurement electrode 13. The device 11 combines the advantages of a symmetrically wired measurement cell (high invulnerability to noise) with the advantages of an asymmetrical measurement cell (small required measurement range).

Since the modulation of the comparison electrode 15 can take place up to the negative power supply voltage limit, and the measurement signal φpH and the reference signal φref can proceed as far as the positive power supply voltage limit, the common mode detection range is almost doubled by the device 11 without the need to change the voltage supply.

In the measurement device 11, the output signal UpH results from the difference of the measurement potential φpH and the reference potential φref. The actual measurement potential φpH which is on the operational amplifier 17 and the actual reference potential φref which is on the operational amplifier 18 follow in turn from the equations:

$$\phi pH=\phi'pH+\phi bez+\phi chem$$

$$\phi ref=\phi'ref+\phi bez+\phi chem$$

where φ'pH and φ'ref being the measured potentials. According to the prior art, the reference potential φbez is equal to 0 V (ground GND) so that the actual potentials result from the sum of measured potentials and the noise potential. It is proposed that the reference potential φbez be adjusted to the negative value of the noise potential φchem so that they mutually eliminate each other and the actual potentials φpH and φref correspond to the measured potentials φ'pH and φ'ref. The reference potential φbez can also be adjusted to the negative value of the sum of the noise potential φchem and the measured reference potential φ'ref, so that the actual reference potential φref is adjusted to a value of zero.

Figure 3:
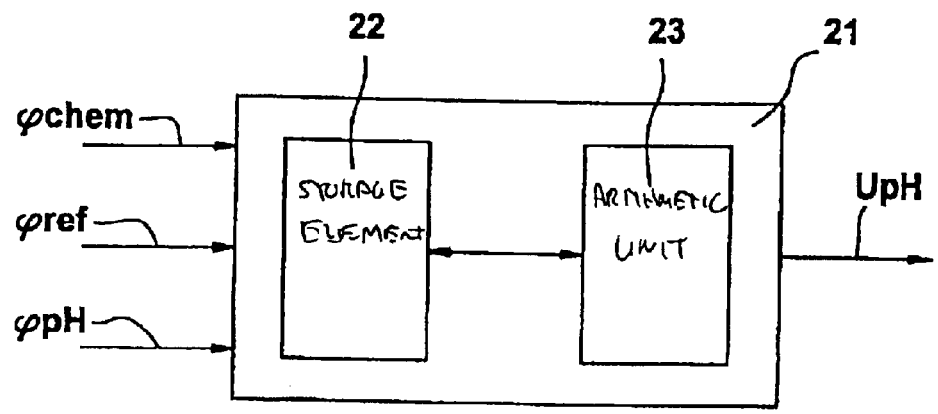
FIG. 3 shows a control unit for the device.

Moreover, a storage element for a control unit of a device for measurement of the concentration of ions, especially hydrogen ($H^+$) ions in a measurement liquid 2, is proposed. The control unit is symbolized in FIG. 1 by a broken line with reference number 21. FIG. 3 shows the structure of the control unit 21 in principle. The control unit 21 has inputs φchem, φref and φpH and delivers the output signal UpH. The storage element is labeled with reference number 22. The storage element 22 stores a computer program which can run on an arithmetic unit 23, especially a microprocessor of the control unit 21 and is suitable for executing the measurement process. The storage element 22 is made for example as a read-only memory, a random-access memory or a flash memory.

Figure 4:
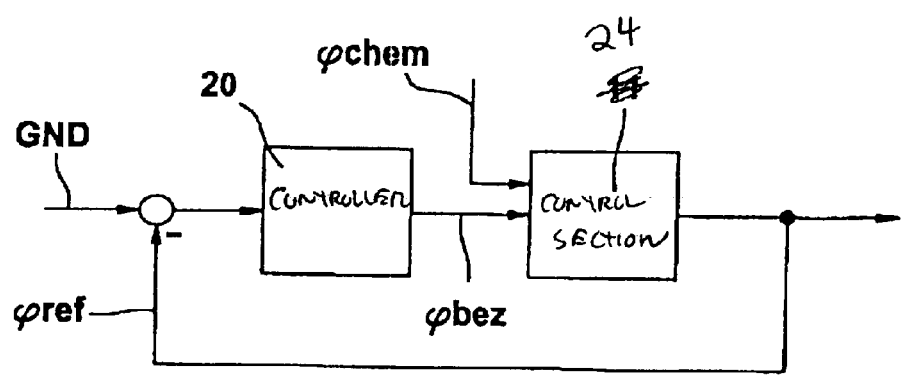
FIG. 4 shows a block diagram of a control implemented with a measurement process as claimed in the invention.

FIG. 4 shows a block diagram of the control implemented with the measurement process. The setpoint is labeled GND. The measured reference signal φref is used as the actual value. The control difference GND-φref is supplied to the controller 20 which generates a corresponding manipulated variable φbez. It is supplied to the control section 24 on which the noise potential φchem acts. In the control section 24, then a corresponding control quantity φref is established.

What is claimed is:

1. A symmetrically wired measurement device for measurement of the concentration of ions, especially hydrogen ($H^+$) ions, in a measurement liquid, comprising:

a pH-sensitive measurement electrode located in the measurement liquid;

a reference electrode located in the measurement liquid;

a comparison electrode located in the measurement liquid which places the measurement liquid at a definable ground reference;

means for forming a difference signal referenced to the ground reference from the difference between a measurement signal (φpH) of said measurement electrode and the reference signal (φref) of said reference electrode, the difference signal being dependent on the ion concentration in the measurement liquid; and compensation means for compensation of the noise potential ($\phi$chem) which arises between said comparison electrode and the measurement liquid,
wherein said compensation means sets a reference potential ($\phi$bez), which is on the comparison electrode, such that the reference signal ($\phi$ref) assumes the value zero.

2. The measurement device as claimed in claim 1, wherein said compensation means comprises a controller element for adjusting the reference potential ($\phi$bez) which is on said comparison electrode to a definable setpoint (GND), the reference signal ($\phi$ref) as the actual value and the setpoint (GND) being on said controller element.

3. The measurement device as claimed in claim 1, wherein said controller element is an operational amplifier, the reference signal ($\phi$ref) is at the noninverting input (+) of said operational amplifier, the ground reference (GND) is at the inverting input (−) of said operational amplifier and the reference potential ($\phi$bez) is at the output of said operational amplifier.

4. A process for the measurement of the concentration of ions, especially hydrogen (H+) ions, in a measurement liquid, including the steps of:

receiving a measurement signal ($\phi$pH) by a pH-sensitive measurement electrode located in the measurement liquid;

receiving a reference signal ($\phi$ref) by a reference electrode located in the measurement liquid;

placing the measurement liquid on a definable ground reference using a comparison electrode located in the measurement liquid;

forming a difference signal referenced to the ground reference from the difference between said measurement signal ($\phi$pH) and said reference signal ($\phi$ref), wherein the difference signal is dependent on the ion concentration in the measurement liquid;

compensating the noise potential ($\phi$chem) which arises between said comparison electrode and the measurement liquid; and setting a reference potential ($\phi$bez), which is on the comparison electrode, such that the reference signal ($\phi$ref) assumes the value zero.

5. The process as claimed in claim 4, wherein the reference potential ($\phi$bez) is controlled depending on the reference signal ($\phi$ref) as the actual value and a definable setpoint (GND).

* * * * *